United States Patent [19]

Lam

[11] 4,199,594
[45] Apr. 22, 1980

[54] N-HALOETHYLTHIO-FURANILIDES AND THEIR USE AS FUNGICIDES AND ACARICIDES

[75] Inventor: Hsiao-Ling Lam, Walnut Creek, Calif.

[73] Assignee: Stauffer Chemical Company, Westport, Conn.

[21] Appl. No.: 40,612

[22] Filed: May 21, 1979

[51] Int. Cl.² .................... A01N 9/28; C07D 307/68
[52] U.S. Cl. ................................ 424/285; 260/347.2
[58] Field of Search ................ 260/347.2; 424/285

[56] References Cited

U.S. PATENT DOCUMENTS 4,117,150  9/1978  Pommer et al. .................... 424/285

*Primary Examiner*—Richard Raymond
*Attorney, Agent, or Firm*—Edwin H. Baker

[57] ABSTRACT

Compounds of the formula

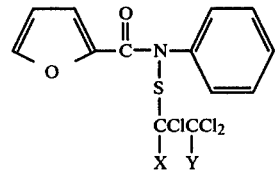

wherein X is chlorine or fluorine and Y is hydrogen or fluorine which are useful as foliar fungicides and acaricides.

6 Claims, No Drawings

N-HALOETHYLTHIO-FURANILIDES AND THEIR USE AS FUNGICIDES AND ACARICIDES

BACKGROUND OF THE INVENTION

This invention relates to certain novel N-haloethylthio-furanilides which are useful as foliar fungicides and acaricides.

The compounds of the present invention have the structural formula

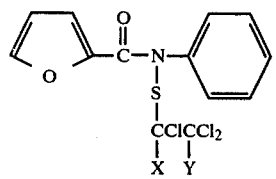

wherein X is chlorine or fluorine and Y is hydrogen or fluorine. Preferably X is chlorine and Y is fluorine.

The compounds of the present invention can be prepared by the following general reactions:

Reaction No. 1

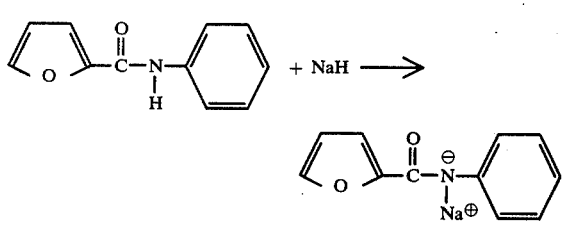

Under a dry nitrogen atmosphere, a mole amount of 2-furanilide is dissolved in dry THF. Next, a slight mole excess of NaH is added with stirring. The mixture is stirred at room temperature for about one-half hour and then refluxed for about two hours and cooled.

Reaction No. 2

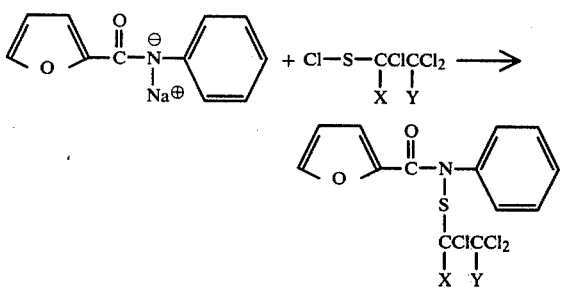

A mole amount of ClSCClXCCl$_2$Y in THF is added dropwise to the reaction mixture of Reaction No. 1 having been cooled with a salt ice bath. The mixture is allowed to warm to room temperature and stirred overnight. The solvent is removed by vacuum stripping and the reaction product is dissolved in methylene chloride. The product is washed twice with water, dried over MgSO$_4$ and evaporated.

Preparation of compounds of this invention is illustrated by the following examples.

EXAMPLE I

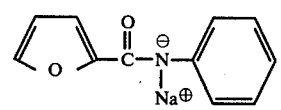

1.68 g (0.09 mole) 2-furanilide and 80 ml tetrahydrofuran were added to a three-necked round bottom reaction flask equipped with a stirrer, reflux condenser and dropping funnel under a dry nitrogen atmosphere. Next, 0.21 g and a small excess of sodium hydride were added and the mixture stirred at room temperature for one-half hour and then refluxed for two hours.

EXAMPLE II

N-1,1,2,2-TETRACHLORO-2-FLUOROETH-YLTHIO-2-FURANILIDE

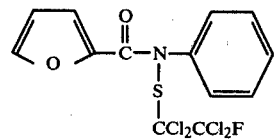

Next, 2.27 g (0.009 mole) of ClSCCl$_2$CCl$_2$F dissolved in 50 ml tetrahydrofuran was added dropwise over one hour to the reaction mixture of Example I which was cooled with a salt ice bath. After the addition, the reaction mixture was allowed to warm to room temperature and the reaction mixture was stirred overnight.

The solvent was removed from the reaction mixture by vacuum stripping. The reaction product was then dissolved in methylene chloride. Water was added to destroy any (unreacted) sodium hydride. The reaction product was washed two times with water and then dried over MgSO$_4$. The product was vacuum stripped to yield 3.33 g of the desired product which was a yellow oil n$_D^{30}$ 1.5844 that later solidified on standing.

The following is a table of certain selected compounds that are preparable according to the procedure described hereto. Compound numbers are assigned to each compound and are used through the remainder of the application.

Table I

| Compound Number | X | Y | n$_d^{30}$ or m.p. |
|---|---|---|---|
| 1[a] | Cl | F | 1.5844 |
| 2 | Cl | H | 85°–89° C. |
| 3 | F | F | 1.5709 |

[a]Prepared in Example II

Foliar Fungicide Evaluation Tests

A. Evaluation for Preventive Action

1. Bean Rust Test

A candidate chemical is dissolved in an appropriate solvent and diluted with water containing several drops of Tween 20®, a polyoxy-ethylene sorbitan monolaurate wetting agent. Test concentrations, ranging from 1000 ppm downward, are sprayed to runoff on the primary leaves of pinto beans (*Phaseolus vulgaris* L.). After the leaves are dried, they are inoculated with a water suspension of spores of the bean rust fungus (*Uromyces phaseoli* Arthur) and the plants are placed in an environment of 100% humidity for 24 hours. The plants are then removed from the humidity chamber and held until disease pustules appear on the leaves. Effectiveness is recorded as the lowest concentration, in ppm which will provide 50% reduction in pustule formation as compared to untreated, inoculated plants. These values are recorded in Table II.

2. Bean Powdery Mildew Test

A candidate chemical is prepared and applied in the same manner as for the bean rust test. After the plants are dry, the leaves are dusted with spores of the powdery mildew fungus (*Erysiphe polygoni* De Candolle) and the plants are retained in the greenhouse until the fungal growth appears on the leaf surface. Effectiveness is recorded as the lowest concentration, in ppm, which will provide 50% reduction in mycelial formation as compared to untreated, inoculated plants. These values are recorded in Table II.

3. Tomato Early Blight

A candidate chemical is prepared and applied in the same manner as the bean rust test except that 4-week old tomato (*Lycopersicon esculentum*) plants are utilized as the host plant. When the leaves are dry, they are inoculated with a water suspension of spores of the early blight fungus (*Alternaria solani* Ellis and Martin) and placed in an environment of 100% humidity for 48 hours. The plants are then removed from the humidity chamber and held until disease lesions appear on the leaves. Effectiveness is recorded as the lowest concentration in ppm, which will provide 50% reduction in number of lesions formed as compared to untreated, inoculated plants. These values are recorded in Table II.

4. Blue Grass Leaf Spot

A candidate chemical is prepared and applied in the same manner as the bean rust test except that four week old Kentucky Bluegrass (*Poa pratensis*) plants are utilized as the host plant. When the leaves are dry, they are inoculated with a water suspension of spores of the blue grass leaf spot fungus (*Helminthosporium sativum*) and placed in an environment of 100% humidity for 48 hours. The plants are then removed from the humidity chamber and held until disease lesions appear on the leaves. Effectiveness is recorded as the lowest concentration, in ppm, which will provide 50% reduction in number of lesions formed as compared to untreated inoculated plants. These values are recorded in Table II.

B. Evaluation for Eradicant Action

1. Bean Rust Test

Untreated bean plants (*Phaseolus vulgaris* L.) are inoculated with spores of the bean rust fungus (*Uromyces phaseoli* Arthur) and placed in an environment with 100% humidity for 24 hours. The plants are then removed from the humidity chamber and held in the greenhouse for two days to allow the disease to become established. A candidate chemical is then prepared and applied in the same manner as in the bean rust test in Evaluation for Preventive Action. Eradicative effectiveness is recorded as the lowest concentration, in ppm, which will provide a 50% reduction in number of pustules appearing on the leaves as compared to untreated inoculated plants. These values are recorded in Table II.

2. Bean Powdery Mildew Test

Untreated pinto bean plants are dusted with spores of the powdery mildew fungus (*Erysiphe polygoni* De Candolle) and maintained in the greenhouse until mycelial growth appears on the leaf surface. A candidate chemical is then prepared and applied in the same manner as for the bean rust test. Four days later the leaves are examined for inhibition of further mycelial growth. Eradicative effectiveness is recorded as the lowest concentration, in ppm, which will provide a 50% inhibition of viable, sporulating mycelium as compared to untreated inoculated plants. These values are recorded in Table II.

Table II

| | Preventive Action | | | |
|---|---|---|---|---|
| Compound Number | Bean Rust | Bean Powdery Mildew | Tomato Early Blight | Blue Grass Leaf Spot |
| 1 | 10 | 500 | 50 | 25 |
| 2 | 50 | 500 | 50 | 20 |
| 3 | 50 | 100 | 50 | 20 |

| | Eradicant Action | |
|---|---|---|
| Compound Number | Bean Rust | Bean Powdery Mildew |
| 1 | 1000 | * |
| 2 | * | * |
| 3 | 1000 | 500 |

*No control at 1000 ppm and not tested at higher concentrations

Acaricidal Evaluation Test

The two-spotted mite (2SM), (*Tetranychus urticae* [Koch]), is employed in tests for miticides. The test procedure is as follows:

Pinto bean plants (Phaseolus sp.) approximately 10 centimeters (cm) tall, are transplanted into sandy loam soil in 3-inch clay pots and thoroughly infested with two-spotted mites of mixed ages and sexes. Twenty-four hours later, the infested plants are inverted and dipped for two–three seconds in 50—50 acetone-water solution of the test chemical. Treated plants are held in the greenhouse, and seven days later mortality is determined for both the adult mites and the nymphs hatching from eggs which were on the plants at the time of treatment. Test concentrations range from 0.05% down to that at which 50% mortality occurs. $LD_{50}$ values are expressed below in Table III under the headings "2SM-PE" (i.e., post-embryonic) and "2SM-Eggs", in terms of percent concentration of the test compound in the solution.

Table III

| Compound Number | 2SM-PE (%) | 2SM-Eggs (%) |
|---|---|---|
| 1 | .002 | .005 |
| 2 | .003 | .01 |
| 3 | .05 | .05** |

**No control at 0.05% and not tested at higher concentrations

The compounds of this invention are generally embodied into a form suitable for convenient application. For example, the compounds can be embodied into pesticidal compositions which are provided in the form of emulsion, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays, propellants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

We claim:

1. A compound having the structural formula

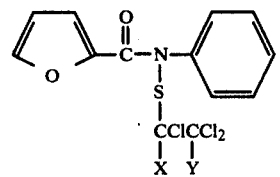

wherein X is chlorine or fluorine and Y is hydrogen or fluorine.

2. The compound of claim 1 wherein X is chlorine and Y is fluorine.

3. The compound of claim 1 wherein X is chlorine and Y is hydrogen.

4. The compound of claim 1 wherein X is fluorine and Y is fluorine.

5. A method of controlling foliar fungi comprising applying thereto an effective amount of a compound having the formula

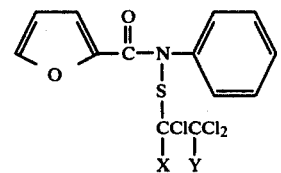

wherein X is chlorine or fluorine and Y is hydrogen or fluorine.

6. A method of controlling acarids comprising applying thereto an acaricidally effective amount of a compound having the formula

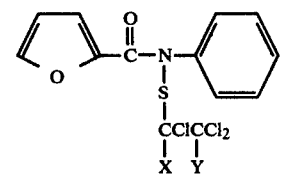

wherein X is chlorine or fluorine and Y is hydrogen or fluorine.

* * * * *